United States Patent [19]

Cheng et al.

[11] Patent Number: 4,619,908
[45] Date of Patent: Oct. 28, 1986

[54] NON-AGED INORGANIC OXIDE-CONTAINING AEROGELS AND THEIR PREPARATION

[75] Inventors: Chung-Ping Cheng, Mt. Kisco; Paul A. Iacobucci, Tarrytown; Edward N. Walsh, New City, all of N.Y.

[73] Assignee: Stauffer Chemical Company, Westport, Conn.

[21] Appl. No.: 685,698

[22] Filed: Dec. 24, 1984

[51] Int. Cl.[4] .......................... B01J 21/04; B01J 21/08
[52] U.S. Cl. ..................................... 502/214; 502/233; 502/235; 502/236; 502/239; 502/343; 502/350; 502/355; 502/405; 423/338
[58] Field of Search ............... 502/214, 233, 234, 235, 502/236, 239, 343, 405, 350, 355; 252/315.01, 315.1, 315.7; 423/338

[56] References Cited

U.S. PATENT DOCUMENTS

| | | | |
|---|---|---|---|
| 1,819,354 | 8/1931 | Behrman | 423/338 X |
| 2,093,454 | 9/1937 | Kistler | 252/6 |
| 2,188,007 | 1/1940 | Kistler | 502/248 X |
| 2,647,875 | 8/1953 | Marisic | 252/448 |
| 3,193,492 | 7/1965 | Plank et al. | 502/236 X |
| 3,672,833 | 6/1972 | Teichner et al. | 23/182 R |
| 3,673,111 | 6/1972 | Hovarth et al. | 502/213 |
| 4,489,172 | 12/1984 | McDaniel | 502/239 |

Primary Examiner—W. J. Shine
Attorney, Agent, or Firm—Vivienne T. White

[57] ABSTRACT

The invention is directed to inorganic oxide-containing aerogels and the method of preparing such oxide-containing aerogels which are characterized by high surface areas and high pore volume. The preparation comprises dissolving the inorganic alkoxide or metal salt in a solvent optionally containing a catalytic amount of an acid or base and hydrolyzing the metal compound which is then further treated with a fluid at or above its critical temperature and pressure to extract the solvent.

34 Claims, No Drawings

NON-AGED INORGANIC OXIDE-CONTAINING AEROGELS AND THEIR PREPARATION

BACKGROUND OF THE INVENTION

1. Field of the Invention

The invention is directed to a method of preparing inorganic oxide-containing aerogels and, in particular, inorganic oxide-containing aerogels in the form of granular material characterized by a high surface area and pore volume.

2. Relevant Art

Inorganic oxide aerogels, specifically metal oxide aerogels, are well known in the art as suitable for a variety of applications such as catalysts, catalyst supports, absorbents, chromatographic column packing, anticaking agents, viscosity enhancers, pigments, opacifiers, as well as ceramics, smoke suppressants, abrasives, dentifrice polishing agents, surfactants and the like.

Examples of some known prior art processes wherein the aerogels prepared in the manner disclosed are utilized as catalysts or catalyst supports are as absorbents in preparing solid phosphoric acid catalysts (as disclosed in U.S. Pat. No. 3,673,111); as a catalyst support for rhodium in the production of olefins and long chained hydrocarbons as discussed in the Journal of Molecular Catalysis, Volume 17, pgs. 219-223 (1983); in the hydrocarbon synthesis from CO and $H_2$ disclosed in U.S. Pat. No. 4,273,724; in the Fischer-Tropsch synthesis described in the Journal of Molecular Catalysis,Vol. 17 (1982), pgs. 171-181; as support for catalyst used in the manufacture of phthalic anhydride; and as a catalyst in the decomposition of hydrogen peroxide.

The preparation of aerogels, in general, the silica aerogels, in particular, has been well documented in the art. U.S. Pat. Nos. 2,249,767; 3,672,833; 2,093,454 and 4,327,065 all disclose processes for producing aerogels. In addition, an article entitled *Inorganic Oxide Aerogels* appearing in Advances in Colloid and Interface Chemistry, Vol. 5, pages 245-273 (1976) published by Elsevier Scientific Publishing Co., Amsterdam, also describes methods of producing various aerogels.

It has been known to produce such aerogels by hydrolyzing salts, or alkoxides, in the presence or absence of a catalyst, generally an acid or base, to form a gel which is washed with water and then solvent exchanged with an alcohol prior to conventionally drying in an autoclave at the critical temperature and pressure of the solvent.

In all the prior art processes for preparing organic oxide aerogels, a requirement of the process is the ageing of the gel prior to removing the solvent is disclosed. The gel time or ageing time not only refers to the time for formation of the gel, but additional time to complete the reaction processes which comprise: formation of the alcogel and thereafter the formation of the inorganic oxide material. Co-pending application Ser. No. 565,937 discloses the process of preparing inorganic oxide aerogels wherein the solvent is extracted from the aged aerogel in an autoclave using an extraction fluid.

SUMMARY OF THE INVENTION

It has been discovered that substantially amorphous inorganic oxide aerogels characterized by high pore volume and surface area can be prepared without ageing the gel prior to extraction. The method comprises:

(a) hydrolyzing a compound comprising at least one metal dissolved in a solvent, (b) contacting the hydrolyzed compound in an autoclave with an extraction fluid above the critical temperature and pressure of the fluid to extract the solvent and, optionally (c) drying the inorganic oxide aerogel produced.

Preferably in the practice of the invention after step (b) the autoclave is depressurized at a rate necessary to maintain the temperature above the critical temperature of the fluid for the time necessary to prevent condensation.

The substantially amorphous, solid, dry, metal oxidecontaining product of the disclosed invention has a higher than normal surface area and pore volume.

DETAILED DESCRIPTION OF THE INVENTION

The instant invention is directed to obtaining substantially amorphous inorganic oxide-containing aerogels characterized by high surface area and high pore volume, primarily metal oxide aerogels corresponding to metals of Groups II, III, IV, V, VI, VIIB and Group VIII of the Periodic Table of Elements and aerogels which are combinations of such metal oxides. The term "inorganic oxide-containing aerogels" refers to an aerogel product comprised of amorphous inorganic oxide materials, and such materials containing non-hydrolyzed alkoxy groups and/or amorphous inorganic oxide materials whose outer surface display organic alcohol groups.

The invention's starting material is comprised of one or more inorganic metal alkoxides, or metal salts (hereinafter the term "inorganic alkoxides" covers salts unless otherwise specified) which are dissolved in a solvent and hydrolyzed by means of water, optionally with an added catalyst, to produce alcogels and then solvent exchanged in an autoclave with a fluid above the critical temperature and pressure of the fluid to produce aerogels. For instance, aerogel compositions such as $TiO_2/SiO_2$; $Al_2O_3/SiO_2$; $SiO_2$; $ZnO$, $ZnO/SiO_2$; and $ZrO_2/SiO_2$ can be produced using the method disclosed herein.

In the practice of the invention one or more inorganic metal alkoxides or salts thereof may be used as the starting material for preparing the aerogels. It is, however, preferred to utilize metal alkoxides.

SILICA AEROGELS

Generally $C_1$–$C_5$ alkoxides such as tetramethyl silicate and tetraethyl silicates, and $SiCl_4$.

ZINC AEROGELS

Generally $C_1$–$C_5$ alkoxides as for instance diisopropoxy zinc and chloride salts.

ZIRCONIA-SILICA AEROGELS

Generally $C_1$–$C_5$ alkoxides such as tetra-isopropoxy zirconium, tetra sec-butoxy zirconium, tetraethoxy zirconium, tetramethyl silicate, tetraethyl silicate.

ALUMINA-SILICA AEROGELS $C_1$–$C_5$ alkoxides.

TITANIA-SILICA AEROGELS $C_1$–$C_5$ alkoxides.

ALUMINA AEROGELS $C_1$–$C_5$ alkoxides, and chloride salts of aluminum.

The criteria for the starting material are inorganic metal alkoxides or metal salts which will dissolve in the specified solvent. In any event, the starting material being dissolved will be an alkoxide since the salts of the metals used will be treated to produce the alkoxide prior to hydrolysis. Preparation of metal alkoxides is disclosed in *Metal Alkoxides* by Bradley, Mehrotra and Gaur, Academic Press (1978) incorporated herein by reference. This starting material is dissolved in an organic solvent, preferably an alcohol and most desirably $C_1$–$C_5$ alcohol or isomers thereof. Alcohols such as ethanol, isopropanol and sec-butanol are desirable for use in practicing the invention. In the practice of the invention it is preferable to utilize an alcohol which corresponds to the alcohol of the metal alkoxide being dissolved. Group IIA and B metals tend to form polymeric alkoxides which are insoluble in alcohols after isolation. In such instances it may be necessary to prepare the alkoxide in-situ with the alcohol.

The solvent utilized in the process should be a solvent for the inorganic alkoxide or alkoxides which are utilized; should be miscible in water and, optionally, the added hydrolysis catalyst; and should be soluble in the supercritical fluid. The amount of solvent utilized will determine the density of the finished aerogel.

The dissolved inorganic salt or alkoxide is hydrolyzed by the addition of at least a stoichiometric amount of water. The amount of water added in the process affects the pore size and surface area of the inorganic oxide aerogel formed. The water added should be sufficient to at least liberate the alkoxy groups from the alkoxide. Adding excess (over stoichiometric) amounts of water will accomplish the above.

The added amount of water should be sufficient to enable complete hydrolysis to take place. It is preferable to use deionized water in the practice of the invention to reduce the ion content in the formed gel. In certain applications, for instance wherein the aerogel is prepared for use as a catalyst or catalyst support, deionized water should be used in preparing the aerogel. The stoichiometrically requisite water amount may simply be calculated from the formula of the hydrolysis reaction. In general, the amount of water added should be from 1 to 10 times the stoichiometrically requisite amount, preferably from 1 to 5 times the stoichiometric amount. Too great an excess of water, however, can cause rapid hydrolysis thus resulting in shrinkage in the gel. Further, an over-excess is undesirable since such an excess may not be extracted by treatment with the supercritical fluid. The desirable amount of excess will also vary with the specific aerogel being produced.

The aerogels of the invention can be prepared in acidic, neutral or basic medium generally depending on the acidity or basicity of the metal oxide formed. Since the pH of the gel can be acid or basic depending on the metal utilized, to enhance hydrolysis, a catalytic amount of an acid or base is desirably added in most instances. The addition of a catalytic amount of an acid or base during or simultaneous with the addition of the water affects the pore size and surface area of the product formed as indicated above. Although acidic medium is generally preferred in preparing a number of inorganic oxide aerogels, the type of medium utilized generally depends on the specific inorganic oxide being produced. In the production of aluminum oxide aerogels, for instance, a neutral pH is preferred since an acidic medium was found to cause a loss of pore volume. In the production of titanium oxide aerogels a basic medium causes the $TiO_2$ to precipitate as discrete fine particles with lower surface area and pore volume.

The optional conditions for preparing a specific gel can be easily determined either from known prior art references or without much experimentation in accordance with the method disclosed herein.

Normally, the catalytic amount of the acid or base added in the process is less than 1% by total volume. The addition of excess acid or excess base increased the ions in the gel and such excess was found to impede the formation of the gel as is further discussed below.

Any organic or inorganic acid or base can be utilized, as for instance, HCl, HF, acetic acid, $NH_3$, diethylamine, $HNO_3$ and $H_2SO_4$, all of which are suitable for use in practicing the invention. Certain acids or bases may, however, be more desirable for preparing specific inorganic oxides in the process of the invention. It is well within the knowledge of one skilled in the art to determine the more favorable conditions for producing the desired aerogel without undue experimentation.

An excess in acid or base may cause rapid precipitation of the gel which would also cause shrinkage in the gel or cause excess ions to remain in the final product which can be undesirable.

The hydrolysis of the alkoxide, or metal salt is generally conducted at room temperature. However, the hydrolysis can occur at temperatures of from about $-20°$ C. to about the boiling point of the solvent and preferably at temperatures of from about $-20°$ C. to about $30°$ C.

Generally in the process of the invention, the concentration of the inorganic alkoxide or metal salt should be from about 2% to about 50% (based on the total volume of the reactants utilized). Preferably the concentration should be from about 2% to about 25%. At lower concentrations, gelation will not generally occur and at higher concentrations it is contemplated that a heavier gel will be formed having less pore volume and surface area. It is desirable to produce a gel having the least amount of solids using the most amount of solvent to achieve the highest surface area and pore volume possible.

Hydrolysis is conducted with cooling of the components where necessary either prior to or during the reaction proper. In the hydrolysis reaction an acid intermediate is formed and is hydrated and polymerized, with water liberated. In this manner, a number of small kernels are formed whose interiors are constituted by amorphous inorganic oxide and whose outer surface displays organic alcohol groups. In due course the kernels are coupled by inorganic oxide linkages to form a space net which will be generally completed only after some ageing. After hydrolysis depending on the specific inorganic oxide being prepared, the hydrolyzed material is extracted to remove the solvent therefrom. Unlike the prior art processes no gelation or ageing time is allowed. The gelation material from which the solvent is extracted may therefore be comprised of varying amounts of amorphous inorganic oxidecontaining alcogel material and such material containing non-hydrolyzed alkoxy groups and/or amorphous inorganic oxide material whose outer surface display organic alcohol groups.

Prior to extracting the solvent it is desirable to remove excess solvent from the alcogel to decrease the amount of solvent that must be extracted. This process step, while not a requirement of the process, is prudent to reduce processing time and energy requirements. Simply decanting the excess liquid is sufficient.

In the practice of the invention the various components (metal salt or inorganic alkoxide, water and optionally the catalytic amount of the acid or base) are charged to a reaction vessel in varying sequence dependent of the specific inorganic oxide aerogel being produced. Generally, the alkoxide, or metal salt thereof is initially dissolved in the mixture comprised of the solvent, water and acid or base. In some situations, however, it may be more desirous to slowly dissolve the alkoxide, or metal salt in the solvent prior to adding water and the specified amount of acid or base to form the gelled or colloidal material. As previously indicated, the structure of the gel can be altered by adjusting the pH of the solution.

The treatment of the alcogel for conversion to aerogel constitutes the second major step and is carried out, in practice, in an autoclave.

The solvent ladened gel or colloid which is formed in the practice of the invention is placed in an autoclave where it is contacted with a fluid above its critical temperature and pressure by allowing the supercritical fluid to flow through the material solid and liquid until the solvent is no longer being extracted by the supercritical fluid.

In performing the invention, various fluids can be utilized at their critical temperature and pressure. For instance, fluorochlorocarbons typified by Freon ® brand fluorochloromethanes and ethanes, ammonia, sulfur dioxide, nitrogen oxide, methane, ethane, propane, butane and the like and carbon dioxide, are all suitable for use in practicing the invention, typically gases at atmospheric conditions i.e., room temperature and pressure are used. Carbon dioxide is the preferred critical fluid for the invention. The criteria for the extraction fluid is that it be inert to the metal oxide, dissolve the alcohol or solvent being removed and preferably have a low critical temperature, pressure, and toxicity, and preferably be nonflammable. In addition the critical temperature and pressure of the extraction fluids is below that of the solvent being extracted.

During the extracting process in the autoclave the extraction fluid is constantly being recovered and replaced by clean fluid. The clean fluid can be fresh extraction fluid or recycled extraction fluid which has been treated to remove contaminants. The recovered fluid can be visually checked to determine whether the extraction process has been completed by allowing some of the exiting fluid to escape. If condensation occurs (alcohol) it indicates the need for further extraction, therefore, the extraction process has not been completed. After extraction is completed, optionally the solid is then further contacted with the fluid above the critical temperature and pressure for an additional period of time to insure complete removal of alcohol and substantially all water (only surface water remaining) after which the rate of depressurization of the autoclave is preferentially maintained to keep the temperature at or above the critical temperature of the supercritical fluid.

In some instances it may be necessary to wash the precipitated gel or colloid prior to treatment in the autoclave. The washing is generally necessary to remove free ions when the starting material is a metal salt. The washing also can be considered a solvent exchange where the solvent is exchanged for the water. In such instances the washing solvent must be soluble in the supercritical fluid at conditions near or above the critical temperature and pressure of the fluid. In such instances it is preferable to use the same solvent used to dissolve the alkoxide or metal salt.

The inorganic oxide aerogel after completion of the extraction process is dried at a temperature of from about 80° C. to about 100° C. to remove surface water from the final product since the extraction process does not remove all the water present. The inorganic oxide-containing aerogel which are obtained after extraction in general comprise the amorphous inorganic oxide material, amounts of the inorganic oxide containing non-hydrolyzed alkoxy groups and/or amorphous inorganic oxide material whose outer surface display organic alcohol groups. Depending on the specific metal oxide aerogel being prepared varying amounts of the amorphous inorganic oxide and amorphous inorganic oxide material, whose outer surface display organic alcohol groups are obtained. This is because gelation occurs almost immediately in the preparation of some metal oxide aerogels while in others complete gelation or conversion to inorganic oxide occurs only over a period of several hours.

The solid, dry, granular, inorganic oxide which remains after treatment in the manner disclosed herein exhibited a higher than normal surface area and pore volume. The density of the supercritical fluid used to extract the solvent when necessary should have a density corresponding to the density of the alcohol being removed thus causing the density gradient between the fluid and solvent to be substantially nil. Lowering the temperatures or increasing the pressure will increase the density of the supercritical fluid, though the temperature must of course remain above the critical temperature of the fluid, preferably at $T=1.1$ Tc which is the minimum heat requirement that should be maintained. Tr (1.1) is the reduced temperature expressed as the absolute temperature over the critical temperature. By varying the temperature and pressure, therefore, it is possible to vary the pore size, pore volume and surface area of the aerogel produced.

The sodium content of the aerogel products produced in the manner disclosed is limited to that introduced as contaminants in the reactants used in the preparation. The sodium content of the silica aerogels produced, for instance, was found to be less than 100 ppm and in general ranged from 50 to 90 ppm and the sodium content of an alumina aerogel produced as disclosed was 269 ppm.

Although the inorganic oxide-containing aerogel product of the invention is primarily obtained as a granular material, it is possible to obtain inorganic oxide aerogels in a monolith form. In such instances, however, the flow of the supercritical fluid should be extremely slow and the heat-up and cool-down time should be prolonged.

The following embodiments are provided as examples of preparing various aerogels in accordance with the invention and are not to be considered as limiting the scope of the present disclosure. It is contemplated that aerogels comprising more than one inorganic oxide having varying compositional ranges are within the scope of the invention.

The aerogels prepared in accordance with the processes disclosed herein can be utilized as porous inert carrier material (support) in the polymerization and copolymerization processes wherein a catalyst is impregnated on the support. Such a process is disclosed in U.S. Pat. No. 4,379,759 to Goeke et al., incorporated herein by reference.

Various methods of impregnating the aerogel supports are known in the art. Two such methods are described in U.S. Pat. No. 4,379,759 at Col. 8, line 50 to Col. 10, line 5.

In preparing the polymerization catalyst disclosed in U.S. Pat. No. 4,379,759 the aerogel carrier material is dried by heating to a temperature of greater than 600° C. A precursor catalyst composition comprising a titanium compound and a magnesium compound is impregnated into the carrier material by dissolving the precursor compound in an electron donor compound and admixing the dissolved compound with the carrier or by adding the support to a solution of the chemical raw materials used to form the precursor compositions in an electron donor. Excess solvent or electron donor is removed by drying. Thereafter, the precursor compound is activated by dry blending outside the polymerization reactor the impregnated precursor composition with an activator compound at a temperature of <50° C. Another method of activation is by partially activating outside the polymerization reactor in a hydrocarbon solvent slurry followed by drying the resulting mixture to remove the solvent at from 20° C. to 80° C. and feeding the partially activated precursor composition to the polymerization reactor where activation is completed with additional activator compound.

Electron donors in the process are said to preferably be methyl formate, ethyl acetate, butyl acetate, ethyl ether, hexyl ether, tetrahydrofuran, dioxane, acetone and methyl isobutyl ketone. Preferable activating compounds are said to include $Al_3(C_2H_5)_3$, $Al(C_2H_5)_2Cl$, $Al(i-C_4H_9)_3$, $Al_2(C_2H_5)_3Cl_3$, $Al(i-C_4H_9)_2H$, $Al(C_6H_{13})_3$; $Al(C_8H_{17})_3$, $Al(C_2-H_5)_2H$ and $Al(C_2H_5)_2(OC_2H_5)$. The instant invention is particularly useful in olefin polymerization processes.

In addition to being used as supports for polymerization catalysts, the inorganic oxide-containing aerogels of the present invention have a variety of uses as catalyst supports in numerous other chemical processes some of which were previously mentioned and are briefly described below.

In hydrogenation processes, as for instance the indirect liquefaction of coal, the Fischer-Tropsch process catalysts, such as nickel, ruthenium, platinum, palladium, molybdenum, and rhodium are carried on a granular support material such as titanium oxide. The support can be impregnated with the required quantity of catalyst and air dried and reduced in a flow of $H_2$ at the desired temperature before use.

In gas phase isomerization, reforming processes, it is known to use molybdena-alumina catalysts or platinum or platinum-rhenium catalysts and other bimetallic catalysts such as platinum-rhenium, and platinum-palladium. High surface area carrier material is impregnated with an aqueous solution containing the required amount of the salts of the catalytic metal or metals. The carrier is dried and reduced in hydrogen at an elevated temperature.

Gas phase oxidation processes such as the oxidation of naphthalene and xylenes to phthalic anhydride utilize catalytic carrier materials such as the inorganic oxidecontaining aerogels of the present invention. The desirable catalysts utilized in these processes are $V_2O_5$, $MoO_3$, Ag, Cu, $PCl_3$ and $Bi_2O_3$.

The crystal structure of the prepared metal oxide aerogels are substantially amorphous. By the term "substantially amorphous" it is meant that the aerogels are generally amorphous in structure except that the titania and titania containing aerogels were found to contain a minor amount of crystallinity.

EXAMPLE

An 87.5 ml amount of isopropanol was mixed with 19 ml of deionized-water, one drop of aqueous HCl, and two drops of aqueous hydrofluoric acid. 1.8 ml of tetraethyl orthosilicate (TEOS) was added to the acidic solution and allowed to stir for about 10 minutes. The pH was then adjusted to 4.5 and 50 ml of tetraisopropyl titanate was rapidly added to the stirring solution. A fibrous gel resulted.

After one hour the gel was placed into a one-liter autoclave where it was contacted with supercritical $CO_2$ at 40° C. and 3500 psig (246.1 Kg/cm$^2$) at a rate of about 2 lbs./hr. of (0.907 Kg/hr) supercritical $CO_2$. The apparent tapped bulk density of the final titania was about 0.43 g/cc. The final product has a surface area of 668 m$^2$/g as determined by $N_2$ BET adsorption.

What is claimed:

1. A method of preparing inorganic oxide-containing aerogels comprising:
   (a) hydrolyzing a compound comprising at least one metal dissolved in a solvent, to produce a gel;
   (b) contact the hydrolyzed compound with an extraction fluid above the critical temperature and pressure of the fluid to extract the solvent and optionally,
   (c) drying the gel.

2. The method of claim 1 further comprising depressurizing after step (b) at a rate necessary to maintain the temperature above the critical temperature of the fluid for the time necessary to prevent condensation and to obtain the solid dry aerogel.

3. The method of claim 1 wherein the metal is selected from Groups II to VI, Group VIIB and Group VIII of the Periodic Table of Elements.

4. The method of claim 3 wherein the metal is silicon.

5. The method of claim 3 wherein the metal is titanium.

6. The method of claim 3 wherein the metal is aluminum.

7. The method of claim 1 wherein the compound is an alkoxide.

8. The method of claim 1 wherein the compound is a salt.

9. The method of claim 1 wherein the hydrolysis is conducted by the addition of a stoichiometric amount of water.

10. The method of claim 9 wherein the water added is from about 1 to about 10 times in excess of the stochiometric amount.

11. The method of claim 10 wherein the water added is from about 1 to about 5 times in excess of stoichiometry.

12. The method of claim 1 wherein the hydrolysis is conducted in the presence of a catalyst.

13. The method of claim 12 wherein the catalyst is an acid.

14. The method of claim 12 wherein the catalyst is a base.

15. The method of claim 1 wherein the gel is washed prior to extraction.

16. The method of claim 15 wherein the gel is washed with a solvent.

17. The method of claim 16 wherein the solvent is a $C_1$ to $C_5$ alcohol.

18. The method of claim 1 wherein the extraction fluid has a low critical temperature and pressure.

19. The method of claim 18 wherein the fluid is $CO_2$.

20. The method of claim 1 wherein the solvent used to dissolve the metal containing compound is a $C_1$–$C_5$ alcohol.

21. The method of claim 20 wherein the alcohol is ethanol.

22. The method of claim 20 wherein the alcohol is isopropanol.

23. The method of claim 20 wherein the alcohol is sec-butanol.

24. The method of preparing inorganic oxide-containing aerogels comprising hydrolyzing a metal alkoxide dissolved in a solvent, contacting the hydrolyzed metal compound with an extraction fluid at not less than the critical temperature and pressure of the extraction fluid such that the solvent is extracted and drying the gel to obtain the dried aerogel product.

25. A method of preparing inorganic oxide-containing aerogels comprising hydrolyzing a metal containing compound dissolved in a solvent, contacting the hydrolyzed metal compound with an extraction fluid at not less than its critical temperature and pressure such that the solvent is extracted, drying the gel to obtain the dried aerogel product.

26. The method of claim 25 further comprising depressurizing after extraction of the solvent at a rate necessary to maintain the temperature above the critical temperature of the fluid for the time necessary to prevent condensation and to obtain the solid dry aerogel.

27. A granular inorganic oxide-containing aerogel product, produced by the method of claim 1.

28. A granular inorganic oxide-containing aerogel produced by the method of claim 25.

29. The inorganic oxide-containing aerogel of claim 27 wherein the product is alumina.

30. The inorganic oxide-containing aerogel of claim 27 wherein the product is a zinc oxide aerogel.

31. The inorganic oxide-containing aerogel of claim 27 wherein the product is a silica-titania complex.

32. The inorganic oxide-containing aerogel of claim 27 wherein the product is a zirconia-silica complex.

33. The inorganic oxide-containing aerogel of claim 27 wherein the product is a silica-alumina complex.

34. In a method of manufacturing solid phosphoric acid catalyst utilizing an absorbent, the process comprising using as the absorbent a siliceous inorganic oxide aerogel prepared by the method of claim 1.

* * * * *